(12) United States Patent
Colavizza et al.

(10) Patent No.: US 7,288,370 B1
(45) Date of Patent: Oct. 30, 2007

(54) BAKER'S YEASTS AND STRAINS FOR THEIR PREPARATION

(75) Inventors: Didier Colavizza, Conde sur l'Escaut (FR); Arnaud Deniaud, Marco en Baroeul (FR)

(73) Assignee: Lasaffre et Cie, Paris (FR)

( * ) Notice: Subject to any disclaimer, the term of this patent is extended or adjusted under 35 U.S.C. 154(b) by 0 days.

(21) Appl. No.: 09/716,639

(22) Filed: Nov. 20, 2000

(51) Int. Cl.
*C12Q 1/68* (2006.01)
*C12N 1/00* (2006.01)
*A23C 9/12* (2006.01)

(52) U.S. Cl. .................. 435/6; 435/255.1; 435/942; 426/62

(58) Field of Classification Search .................. 426/62; 435/440, 471, 477, 483, 243, 254.1, 254.21, 435/255.1, 255.2
See application file for complete search history.

(56) References Cited

U.S. PATENT DOCUMENTS

| | | | |
|---|---|---|---|
| 4,222,972 A * | 9/1980 | Caldwell | 261/121.1 |
| 4,328,250 A | 5/1982 | Clement et al. | |
| 4,396,632 A | 8/1983 | Clement et al. | |
| 5,741,695 A | 4/1998 | Hennette et al. | |
| 5,801,049 A | 9/1998 | Endo | |

FOREIGN PATENT DOCUMENTS

AU 609030 9/1987

OTHER PUBLICATIONS

Prakash et al. Mutation Researchj 451: 13-24, 2000.*
www.bread-bakers.com/archives/digests/v096n024.txt. 1996..*
Satoshi Nakagawa and Kozo Ouchi, "Construction from a Single Parent of Baker's Yeast Strains with High Freeze Tolerance and Fermentative Activity in Both Lean and Sweet Doughs", Applied and Environmental Microbiology, Oct. 1994, p. 3499-3502, vol. 60, No. 10, XP-002119705.
Philip Meaden, "PADding out POF gene", FERMENT, vol. 7, No. 4, 1994, pp. 229-230, XP002189235.
Rutger Van Rooden and Paul Klaassen, "Genetic Modification in the Food Industry: A Strategy for Food Quality Improvement", 1998, Blackie, London, p. 158-173.
European Search Report dated Mar. 11, 2002 for EPA No. 01402969.8-2405.

* cited by examiner

*Primary Examiner*—Nancy Vogel
*Assistant Examiner*—Michele K. Joike
(74) *Attorney, Agent, or Firm*—Sughrue Mion, PLLC

(57) ABSTRACT

New baker's yeasts which have good general performances in not-delayed bread-making, i.e., in bread-making processes which do not comprise a freezing or a deep-freezing step, are resistant with respect to the stress caused by freezing when they are used in sweetened doughs and do not give rise to the appearance neither of bad taste, nor of off-flavors in the presence of cinnamon.

45 Claims, 1 Drawing Sheet

BAKER'S YEASTS AND STRAINS FOR THEIR PREPARATION

BACKGROUND OF THE INVENTION

The present invention relates to new baker's yeasts or bread-making yeasts. It also relates to strains for the preparation of said baker's yeasts.

In the USA, the trade of frozen doughs, notably of sweet doughs such as frozen doughs intended for bakery products called "Rolls", for Danish sweet pastries or for similar sweet fermented and baked products is quickly expanding; however, freezing involves an important stress for the yeast.

In the USA, small breads or fermented pastries are very often aromatized (flavored) with cinnamon; this spice contains cinnamic acid and cinnamaldehyde; these chemical compounds can be metabolized by yeasts which leads to the appearance of bad taste and of bad flavors, also called "off-flavors".

Baker's yeasts are known that are resistant to the stress caused by freezing or deep-freezing and which can be used in frozen doughs without the necessity of increasing to an important extent the amount of yeast as is necessary when using conventional baker's yeasts that are not resistant to the stress caused by freezing or deep-freezing. Baker's yeasts resistant to freezing have been developed in Europe and in Japan.

Also known are baker's yeasts which can be used without formation of off-flavors, in the manufacture of bakery products comprising cinnamon. Such baker's yeasts, which do not give rise to the appearance of off-flavors in the presence of cinnamon, are commonly marketed in the USA.

PRELIMINARY ASPECTS OF THE INVENTION

The new baker's yeasts of the present invention have the properties of the two types of baker's yeasts here-above discussed.

These new baker's yeasts are characterized by the fact that:
  they have good general performance in not delayed bread-making processes, i.e., in bread-making processes that do not comprise a freezing or deep freezing step,
  they are resistant to the stress caused by freezing when they are used in sweet doughs and,
  they do not give rise to the appearance of bad taste or of off-flavors in the presence of cinnamon.

Indeed this property of not giving rise to the appearance of bad taste or of off-flavors is essential for a baker's yeast and must be verified in any breadmaking process wherein the said baker's yeast is intended to be used.

In the tests $A_1$, $A_5$ and $A_6$ carried out with the fermentometer of Burrows and Harrison, described in column 5 of U.S. Pat. No. 5,741,695 of Apr. 21, 1998, the entire disclosure of which is incorporated by reference, good general performance in not delayed bread-making processes obtained with the new baker's yeasts of the present invention led to the following gas releases:
  in test $A_1$, at least 150 ml in 2 hours,
  in test $A_5$, at least 90 ml in 2 hours,
  in test $A_6$, at least 80 ml in 2 hours.

In other words, the new baker's yeasts of the present invention are characterized by the fact that in not delayed bread-making processes, they give rise in the fermentometer tests $A_1$, $A_5$ and $A_6$ carried out with the fermentometer of Burrows and Harrison to gas releases which are at least equivalent to those obtained with a control yeast produced according to a conventional process starting from the strain deposited at the "Collection Nationale de Cultures de Microorganismes" (CNCM), Institut Pasteur under the number CNCM I-2412, on Mar. 22, 2000, which is representative of the strains commonly used in the USA for the manufacture of baker's yeasts.

A conventional process of baker's yeast manufacture is a process described in the Chapter 6: "Baker's Yeast Production" of the handbook "Yeast Technology", Second Edition, Reed and Nagodawithana, An Avi Book published by Van Nostrand Reinhold, 1991.

The resistance toward stress caused by freezing of the new baker's yeasts according to the invention is characterized:
  on the one hand by the fact that, when used in doughs corresponding to formulations of sweet Danish pastries, i.e., to doughs comprising about 18% sugar (sucrose) by weight with respect to the flour used and comprising fats, the total gas releases recorded after freezing and thawing of the said doughs after at least 100 days are higher by at least 20%, preferably by at least 30% and still more preferably by at least 40% than the total gas releases recorded under the same conditions when using a control yeast obtained conventionally starting from a control strain such as the strain CNCM I-2412, and
  on the other hand by the fact in the above-defined use, the proof time of the said sweet Danish pastry dough, frozen and thawed after at least 100 days, is lower by at least 10%, preferably by at least 15% and still more preferably by at least 20% than that measured under the same conditions when using the above-defined conventional control yeast.

In these comparisons the control yeast must have the same form as the new baker's yeast of the present invention that is tested.

Preferably, the total gas releases on the dough pieces are measured using the zymotachygraphe CHOPIN® for 2 hours and 30 minutes at 27° C. and the proof times are measured at 35° C.

Proof time as used herein is the length of time for which a moulded dough piece is held in the final proofer prior to baking so it can attain the desired degree of aeration or volume increase. See, *The Handbook of Basic Technical Baking Terminology* by E. J. Pyler.

Strains of Yeast Used in the Invention

It is recalled that the zymotachygraphe CHOPIN® or CHOPIN® zymotachygraphe is a conventional apparatus known to those skilled in the art for measuring the gaseous release of a dough ball or piece. This apparatus is notably described in a detailed manner in chapter VII B "Appreciation du pouvoir fermentaire" (appreciation of the fermenting power), §6.5 "Le Zymotachygraphe" (CHOPIN, 1973), pages 461 to 463 in the manual "Guide pratique d'analyses dans les industries des céréales", B. Godon and W. Loisel, Technique et Documentation (Lavoisier) 1984, ISBN 2-85206-081-7 Collection 2-85206-230-5. The fermentometer of Burrows and Harrison is the object of §6.1 of this Chapter VIIB, pages 454 to 460.

For the preparation of the new baker's yeasts according to the invention, it is possible to use two strains which were deposited on the 24 of Mar. 2000 according to the Budapest Convention with the "Collection Nationale de Cultures de Microorganismes" (CNCM), Institut Pasteur, 28 rue du Docteur Roux, 75724 PARIS CEDEX 15, FRANCE, under the numbers:

I-2421 (strain L17)

I-2422 (strain L35).

Strain L17, for the reason of its possible industrial use was deposited under the number CNCM I-2421 and had been cited in a different context in U.S. Pat. No. 5,741,695, but the strain had been considered at that time as presenting no interest as a baker's yeast strain due to its thigh invertase content. It was not deposited before the 24 Mar. 2000 with a Public Culture Collection Center (deposit according to the Budapest Convention). It has always been kept in the private and confidential collection of the Lesaffre Group in its research laboratories located at 59700 Marcq-en-Baroeul in France without being commercially or publicly used and without being accessible to third parties. Consequently, this strain is a novel baker's yeast strain.

Strain L35, deposited under the number CNCM I-2422 was obtained by mutation starting from strain L17; that strain has never been cited in a prior art document, and is also a novel baker's yeast strain.

These two strains were selected from a great number of strains among the strains of the private collection of the Lesaffre Group using three series of systematical selection tests. The confidential and private collection of the Lesaffre Group contains numerous strains which were constructed, notably according to the reproducible construction processes of new strains disclosed by the U.S. Pat. Nos. 4,396,632 and 5,741,695. The entire disclosures of these two US patents are incorporated herein by reference.

In these different series of tests, the control strain is the one which was deposited with the "Collection Nationale de Cultures de Microorganismes", under the number I-2412. That strain is representative of the strains which are commonly used in the USA for the manufacture especially of baker's yeasts intended for the breadmaking of products of the sweet roll type and of Danish pastries.

Selection Tests

The control strain and the various tested strains were cultivated on cane molasses in pilot installations. The scheme of the cultivation on cane molasses, used here, is the one disclosed in example 3 of U.S. Pat. No. 5,741,695 from line 40, column 12, to line 26, column 13, wherein the strains were propagated in several stages of aerobic multiplication and the fresh yeast was collected, washed and filtered, using the conventional materials employed in yeast production and the conventional manufacturing processes, such as the materials and processes described in "Yeast Technology" by Gerald Reed and Henry J. Pepler (1973), the Avi Publishing Company Inc. or in the chapter "Production of Baker's Yeast", Gerald Reed, published by Prescott and Dunn's Industrial Microbiology, 4$^{th}$ Edition, edited by Gerald Reed, the Avi Publishing Co., Inc., second printing 1983.

Particular care was taken to ensure that all nutriments required in small quantities in yeast, minerals, (macroelements and oligoelements) and vitamins (biotin and Group b vitamins) were present at least in the largest quantities recommended in the reference work cited above. These tests are in general carried out as indicated in French Patent No. 7739149, European Pat. No. 0008554 and U.S. Pat. No. 4,396,632. Particular care was taken to obtain the yeasts in a well washed condition and to chill the cream and the filtered yeasts rapidly to 2° C.

The last stage of multiplication of the yeast resulting in a highly active compressed fresh yeast is more specifically carried out as follows:

dilution of the culture medium at the end of commercial multiplication:

$$\frac{\text{Weight of yeasted wort in the vat}}{\text{Quantity of molasses with 50\% total sugar content expressed as sucrose}} = 5.2$$

These tests are preferably carried out with a mixture of 90% of beet molasses and 10% of cane molasses, these molasses (beet molasses and blackstrap molasses) should be of good quality, i.e., having high purity and not containing inhibitors or toxic substances for yeasts. It shall be particularly checked by tests on control cultivations that molasses do not contain toxic additives sometimes added during the extraction and purification work of sugar in sugar factory. The sugar of the beet molasses is measured by Clerget's method (determination of sucrose by double polarization), the sugar of the cane molasses is determined by enzymatic measurement of the sucrose, glucose and fructose actually present, and the totality of these sugars is calculated in sucrose equivalents;

mean hourly rate of multiplication in the last multiplication cycle of 14 hours: 1.18 to 1.20.

maximum proportion of yeast buds collected: 10%.

proportion of nitrogen/yeast solids content collection: 9% (8.6 to 9.2).

proportion of $P_2O_5$/yeast solids content collected: 3%.

Fresh baker's yeasts having a dry matter content of about 32% were obtained. The nitrogen content with respect to the dry matter of these fresh yeasts is adjusted between about 8.2% and about 8.5%.

Test S1

The first selection test, S1, consists of searching the various fresh baker's yeasts obtained with the various tested strains that give rise in tests $A_1$, $A_5$ and $A_6$ carried out with a fermentometer of Burrows and Harrison as disclosed in column 5 of U.S. Pat. No. 5,741,695 which is incorporated herein by reference, to results which are at least 150 ml in test $A_1$ in two hours, at least 90 ml in test $A_5$, in two hours and at least 80 ml in test $A_6$, in two hours.

These results, in absolute value, concerning gas releases or proof times, must always be compared with respect to at least a control. As a matter of fact, the principles indicated in example 6 of U.S. Pat. No. 5,741,695, columns 19 and 20, and especially column 20, lines 50 to 57 have a general value.

Test S2

The second systematical selection test, S2 consists of the examination of their behavior with respect to cinnamon, of fresh yeasts issued from the first selection test, i.e. fresh yeasts, which, in the tests $A_1$, $A_5$ and $A_6$, give at least the hereabove defined results.

In the second selection test, S2, quantities of 150 mg of dry matter of each of the fresh baker's yeasts fermented for 4 hours at 30° C. under weak agitation in two 125 ml flasks that are not hermetically closed and that contain respectively 20 ml of each of first and second sweet nutrient solution. The two nutrient solutions, buffered to pH 5.5, contain per 1000 ml: 4.7 g $(NH_4)_2HPO_4$, 2 g Mg $SO_4 7H_2O$, 0.8 g KCL, 10 ml vitamins solution and 150 ml citrate buffer. The 10 ml solution of vitamins contains 4 mg thiamin (B1 vitamin), 4 mg pyridoxyn (B6 vitamin) and 40 mg nicotinic acid. The 150 ml citrate buffer contains 14.14 g of trisodium citrate and citric acid necessary to adjust the pH to 5.5. The first sweet nutrient solution or control solution consists of the nutrient solution to which is added 6% of sorbitol, 0.25% of yeast extract and 6% of glucose. The second sweet nutrient solution consists of the nutrient solution to which is added 6% of sorbitol, 0.25% of yeast extract, 6% of glucose and 0.04% of cinnamic acid. The percentages are expressed in weight with respect to the total or final volume of sweet nutrient solutions.

The second test consists in the comparison of the odor of the solution fermented without cinnamic acid with that of the solution fermented in the presence of cinnamic acid. This test of comparison of odors, based on the detection of off flavors due to the decomposition of cinnamic acid is made on the basis of notes given by a jury. The notes given by the jury can be confirmed by analysis of the decomposition rate of cinnamic acid, i.e., by the determination of the cinnamic acid still present at the end of the test and/or by the determination of styrene present in the solution fermented in the presence of cinnamic acid.

The presence of Cinnamic acid and styrene can be measured by chromatographic methods known to those skilled in the art in the fermented solutions centrifuged at 4° C. in order to remove yeast cells. The presence of cinnamic acid can be dosed measured by reverse phase HPLC (High Performance Liquid Chromatography) on C18 column, the elution being realized by a gradient of acetonitrile between 10% and 40% in water, in presence of 0.1% of trifluoroacetic acid (percentages volume/volume), the detection being realized by an U.V. detector at 260 nm. The presence of styrene can be measured by gas chromatography coupled with mass spectrometry. The presence of styrene was measured in a VARIAN® GC 38000 gas chromatograph equipped with column CHROMPACK® CP-Wax 52 CB 30 m*0.25 mm, df:0.5 µm. The sampling method used was based upon static headspace, wherein 3 g of supernatant was placed into 10 ml glass vials which were heated at 35° C. with agitation for the timed equilibrium step (15 min), and the headspace volume of 100 µl was injected into the GC column. The oven temperature of the chromatograph was programmed as follows: 2 min isotherm at 55° C., heated at 5° C./min up to 230° C. Helium was used as carrier gas with a flow rate of 1 ml/min. The styrene was detected by mass spectrometry SATURN 2000 VARIAN®.

This second test shows that most of the baker's yeasts used in Europe, and especially the baker's yeasts which in Europe are considered as efficient on frozen doughs, give rise to the appearance of off-flavors in the presence of cinnamic acid.

At the end of this second test, only baker's yeasts that do not give rise to the formation of off-flavors are selected. Notably, baker's yeasts obtained from the strain L17 (CNCM I-2421) and from the strain L35 (CNCM I-2422) pass successfully this second test.

The control baker's yeast obtained starting from the strain CNCM I-2412 does not give rise to the formation of off-flavors in that test.

The strains CNCM I-2412, CNCM I-2421 and CNCM I-2422 being are three examples of strains which successfully pass this test and consequently they permit calibration of this biological test by comparison.

Test S3

The thus selected strains through the hereabove defined baker's yeast selections are then subjected to a third series of selection tests, S3, which consist in the determination of their resistance against the stress caused by freezing, in other words their qualification for the preparation of baker's yeasts which can be used in the manufacture of frozen dough pieces intended for sweet rolls and for sweet Danish pastries.

The compositions of the sweet rolls and the sweet Danish pastries used in the third series of tests are as follows:

1) Rolls containing 6% of HFCS (high fructose corn syrup) dry matter or 10% of sucrose:

| flour | 100.0 |
|---|---|
| water | 55.0% |
| yeast expressed in dry matter | 1.86% |
| HFCS expressed in dry matter | 6.0% |
| | (or sucrose 10.0%) |
| fats | 5.0% |
| salt | 2.0% |
| dough improver | 2.0% |

2) Sweet Danish pastries:

| flour | 100.0 |
|---|---|
| water | 46.0% |
| yeast expressed in dry matter | 2.72% |
| sucrose | 18.0% |
| fats | 13.0% |
| pulverulent lactoserum | 4.0% |
| salt | 2.0% |
| dough improver | 2.0% |

The percentages are expressed in what is called "baker's percent", that is to say in weight with respect to 100 parts of the total flour used.

The flour used is a US flour having a high gluten content well adapted to bread-making comprising a deep-frozen step.

The dough improver used for the rolls and for the Danish pastries brings gluten, diacetyltartaric esters of monoglycerides (DATEM), ascorbic acid, alpha-amylases and hemicellulases, in amounts permitting to obtain optimized dough pieces for deep frozen and long storages at −20° C.

The conditions of the manufacture of the frozen doughs intended for rolls and for Danish pastries, those of the storage of the frozen doughs until thawing of the frozen doughs and those of the tests to which the dough pieces are subjected are as follows:

mixing, temperature of the dough at the end of mixing: 19° C., separation in balls of 100 g, in a room whose temperature is 19° C., beginning of deep-freezing 35 minutes after the end of mixing, deep-freezing during 35 minutes at −30° C. which provides a temperature at the center of dough pieces of −5° C., storage at −20° C. during 100 days, thawing within 20 hours at 0° C. at the end of each of the storages of 100 days, determination after thawing of the total gas release using the zymotachygraphe Chopin® during 2 hours and 30 minutes at 27° C., proofing and measuring of the proof time at 35° C. on three dough pieces or balls, baking and appreciation of volume and of the scoring of obtained rolls or pastries and notably verification of the absence of any bad taste or any off-flavors.

Within the framework of these tests, baker's yeasts were selected which provided dough pieces of sweet Danish pastries obtained as here-above disclosed and thawed after 100 days at −20° C., which showed the following performances:

total gas release measured using a zymotachygraphe CHOPIN® in 2 hours and 30 minutes at 27° C. at least higher by 20% with respect to that of the pieces obtained under the same conditions using the control yeast conventionally manufactured starting from the strain CNCM I-2412 and stored in the same manner, proof time lower by at least 10% with respect to that of dough pieces obtained and stored under the same conditions but using the control yeast, absence of any bad taste or any off-flavors.

The tests carried out with the dough pieces corresponding to the formulations of sweet rolls confirm the selection because they verify that the desired properties are also obtained with a wide range of sweet pastries.

The two strains selected at the end of these three systematical selection tests are the two strains here-above identified, i.e., the strains deposited at the CNCM under the numbers I-2421 and I-2422.

These two strains have been selected because the yeasts manufactured starting from these strains gave rise with respect to the control yeast to the greatest differences in all the tests of frozen and thawed doughs.

The yeasts obtained with these two selected strains allowed for the production of frozen sweet Danish pastry pieces which, when thawed after 100 days at −20° C., provided a total gas release which was higher by at least 30% when measured with the zymotachygraphe CHOPIN® and a proof time lower by at least 20%, in fact by 25%, with respect to the control yeast used under the same conditions.

These two strains are used to produce yeast creams and fresh yeasts which show a good aptitude for maintaining their properties during storage. These two selected strains CNCM I-2421 and I-2422 also present interesting properties consistent with the fact that they respond well to cultivation processes with discontinuous inflow of molasses as those disclosed in UK Patent No. 1,539,211 or U.S. Pat. No. 4,328,250 with the view of improving the performances of the yeasts in sweet doughs and especially in the fact that they are keeping these higher performances on sweet dough, due to the use of the said cultivation processes, in sweet dough pieces thawed after several months of storage at −20° C. Preferably, the baker's yeasts according to the invention are obtained using such kind of cultivation processes of adaptation to the fermentation of sweetened doughs.

These two strains CNCM I-2421 and I-2422 also have the property of giving frozen intermediate dry yeasts the use of which is particularly interesting for the making of sweet frozen doughs.

The frozen intermediate active dry yeasts are defined as frozen dry yeasts in the form of particles, having an intermediate dry matter, i.e., a dry matter content of from 70 to 80% in weight, preferably 72 to 78%, still preferably 74 to 78%. The frozen intermediate active dry yeasts can be made as described in European Patent No. 0237427 B2 corresponding to Canadian Patent No. 1,299,435 or corresponding to Australian Patent No. 609 030 (document No. AU-B-69781/87), the entire disclosures of which are incorporated by reference.

Different trials carried out with strain CNCM I-2421 cultivated according to a process with discontinuous inflow of molasses during the whole or part of the last cycle of multiplication, have led to frozen intermediate dry yeasts between 70 and 80% dry matter, preferably between 72 and 78% dry matter, giving the following gas releases in tests $A_1$, $A_5$, $A_6$ described in U.S. Pat. No. 5,741,695:

| test $A_1$ | 170 ml to 190 ml in two hours |
| test $A_5$ | 110 ml to 130 ml in two hours |
| test $A_6$ | 115 ml to 140 ml in two hours. |

In these tests A carried out with frozen intermediate active dry yeasts, the 160 mg of yeast solid content (tests $A_1$ or $A_5$) or the 320 mg of yeast solid content (test $A_6$) of frozen intermediate dry yeast are thawed during one hour at room temperature before being mixed with the 15 ml of water as described column 5 of U.S. Pat. No. 5,741,695.

These two strains CNCM I-2421 and CNCM I-2422 can be characterized by using the identification technique of yeast strains using the Polymerase Chain Reaction and based on the amplification of the inter delta zones of the retrotransposon TY1, which is disclosed in the Article "Identifications of Yeast Strains Using the Polymerase Chain Reaction" by F. Ness, F. Lavallée, D. Dubourdieu, M. Aigle and L. Dulau, published in J. Sci. Food Agric. 1993, 62, 89-94.

DESCRIPTION OF THE DRAWINGS

In that respect it appears from FIG. 1 which shows the electrophoresis profiles of amplified DNA sequences of strains L17 and L35 and a profile of digested DNA used as a molecular weight marker, that the strain L17 (CNCM I-2421) presents two supplemental bands with respect to the strain L35 (CNCM I-2422). Taking into consideration the above-indications, it appears that the present invention relates as a new industrial product not only to the baker's yeasts here-above defined but also to the strains deposited under the numbers CNCM I-2421 and I-2422.

DETAILED DESCRIPTION OF THE PREFERRED EMBODIMENTS

Figure 1:
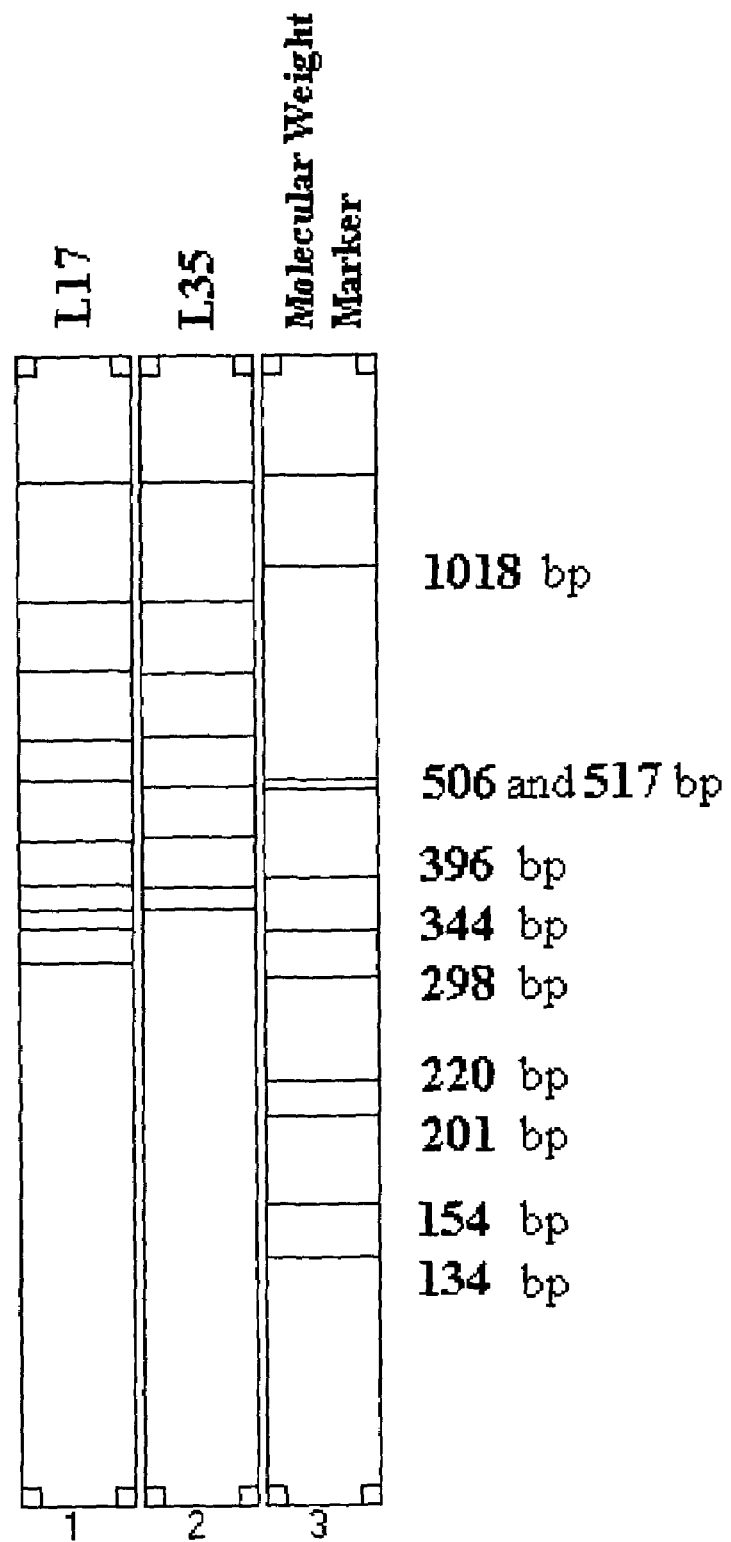

The present invention also relates on the one hand to the use of the two strains CNCM I-2421 and CNCM I-2422 and on the other hand to the use of similar strains to these two strains, for the preparation of baker's yeasts according to the invention in the form of yeast creams, fresh compressed yeasts and active dried yeasts, preferably in the form of frozen intermediate active dry yeasts. It relates also to the new baker's yeasts able to be thus obtained. Similar strains to the two strains CNCM I-2421 and CNCM I-2422 are defined as the strains sharing all the common properties to these two strains and/or as the strains able to be selected by the three series of systematical selection tests hereabove disclosed, i.e., the baker's yeast strains which pass successfully the three systematical selection tests described herein.

As already indicated, baker's yeast strains which have the property of being resistant to the stress caused by freezing were known, but these baker's yeast strains cannot be used without formation of off-flavors in the manufacture of bakery products containing cinnamon.

This default can be corrected and is corrected by the deletion or disruption or inactivation in the genome of said the baker's yeast strains of the PAD1 gene(s) encoding phenylacrylic acid decarboxylase, the enzyme which permits the decomposition of cinnamic acid.

The PAD1 gene is described and characterized entirely by Clausen et al. (1994), Gene 142: 107-112 in an article entitled "PAD1 encodes phenylacrylic acid decarboxylase which confers resistance to cinnamic acid in *Saccharomyces cerevisiae*."This PAD1 gene is also called Phenolic Off Flavors gene or POF gene.

Such a targeted inactivation of the PAD1 gene can be obtained by conventional gene replacement methods (see Rothstein in Guthrie C. and Fiur GR (editors) Guide to Yeast Genetics and Molecular Biology in Methods in Enzymology vol. 194: 281-301) or by employing an integration/excision DNA cassette as described in European Patent Application No. 0 994 192 or in the corresponding U.S. patent application Ser. No. 09/415,216 filed on Oct. 12, 1999, entitled "Yeast Transformation Cassette" or still the Australian Patent Application No. 53572/99, the entire disclosures of which are incorporated by reference.

These patent applications which are incorporated herein by reference disclose integration/excision DNA cassettes which permit the total or partial deletion of the same gene in *Saccharomyces cerevisiae*, leaving in the host strain only yeast DNA. In order to disrupt the PAD1 gene(s), integration/disruption cassette(s) CAS-PAD are constructed on the same principle of the integration/disruption cassettes CAS-SUC disclosed in the example 4 of these patent applications and the cassette(s) CAS-PAD are used to delete or disrupt the alleles of the PAD1 gene by integration(s)/excision(s) as disclosed in the example 4. This strategy consisting of the use of the said integration/excision DNA cassette(s) is preferred because it allows for the inactivation of all copies of the PAD1 gene in a strain containing more than one copy as it is often the case for industrial strains. In addition, this strategy leads to the construction of strains, in which the selectable marker has been eliminated.

This elimination of the selectable marker is very important. Today no baker's yeast is obtained by multiplication of a genetically modified strain and it is generally admitted that only a genetically modified strain stable and without a selectable marker could be acceptable as a baker's yeast strain.

The present invention relates to new baker's yeast strains obtained (or modified) by clean deletion of the PAD1 gene(s) encoding phenylacrylic acid decarboxylase. A clean gene deletion or inactivation is defined as a genetical modification which cuts out the expression of the deleted or inactivated gene(s) (i.e., in the frame of present invention the PAD1 gene(s)), without leading to the expression of a heterologous gene, and preferably without leading to the production of any new compound toward a natural yeast mutant strain which has its said gene(s) disrupted or inactivated.

Another preferred strategy in order to obtain baker's yeast strains which have their PAD1 gene(s) inactivated, consists in mutating baker's yeast strains intended to be modified, by a classic mutagenic treatment giving a cell survival ratio of about 20 to 30% and selecting in a first time the mutated strains which do not show any phenylacrylic acid decarboxylase activity in the presence of cinnamic acid and/or ferulic acid and/or coumaric acid, and notably which show no production of off-flavors (volatile phenols and/or styrene). In a second time, it is verified on the selected mutated cells presenting this property, the no-expression of PAD1 gene(s) by conventional technics as Northern hybridization (described in Molecular Cloning, a laboratory manual, second edition, Sambrook, Fritsch, Maniatis); and it is verified that the mutated (mutant) strains not expressing their gene(s) PAD1 have kept the whole of their interesting properties as baker's yeast strains.

Preferably the present invention relates to baker's yeast strains resistant to the stress caused by freezing and modified by clean deletion (disruption) of the PAD1 gene(s). The starting or host strains are known baker's yeast strains resistant to the stress caused by freezing, such as the baker's yeast strains used to produce the European baker's yeasts for use with frozen doughs cited hereabove, which are modified by clean deletion of the PAD1 gene(s). Still preferably, the starting or host known baker's yeast strains selected in order to be modified by clean deletion of the PAD1 gene(s) contained in their genome, pass successfully the first selection test and the third series of selection tests hereabove disclosed, and the modified strains pass successfully the three series of selection tests hereabove disclosed.

The present invention relates also to the same or equivalent baker's yeast strains obtained by mutation the PAD1 gene(s) of which is(are) inactivated. The mutation process leads to a clean inactivation as hereabove defined. In addition, the present invention relates to all the new baker's yeast strains obtained by clean inactivation of their PAD1 gene(s) whatever method is used for inactivation.

The present invention relates also to new baker's yeasts having the properties hereabove disclosed, which are obtained by a process comprising the use of any of the new modified or mutated baker's yeast strains hereabove disclosed. In a general manner, the present invention relates to the use of the hereabove disclosed modified or mutated baker's yeast strains, obtained by inactivation of the PAD1 gene(s), for the preparation of baker's yeasts in the form of yeast creams, fresh compressed yeasts, frozen intermediate active dry yeasts, and active dry yeasts.

Still, in a general manner, the present invention relates to a process for the preparation of new baker's yeasts according to the invention comprising the conventional cultivation or multiplication of a selected starting strain. Preferably, the new baker's yeasts according to the invention are obtained by the use of a special cultivation process corresponding to a fed-batch process comprising a discontinuous inflow of molasses during the whole or part of the last cycle of cultivation. The invention also has as an object, new baker's yeasts having the new properties hereabove disclosed and obtained or able to be obtained by a process comprising a discontinuous inflow of molasses during the whole or part of the last cycle of cultivation.

Preferably the selected starting strain is strain CNCM I-2421 or I-2422, but the selected strain can be also a similar strain to strains CNCM I-2421 and CNCM I-2422, i.e., a strain sharing all the common properties to these two strains and/or able to be selected as hereabove disclosed, or also a baker's yeast strain obtained by clean inactivation of the PAD1 gene(s).

The present invention also relates to new frozen intermediate active dry yeast products, having between 70 and 80% dry matter, preferably between 72 and 78% dry matter, still preferably between 74 and 78% dry matter. The frozen intermediate active dry yeasts are preferably in the form of rod shaped flowing particles of a diameter less than 3 mm, preferably less than 1 mm, and they are preferably obtained by a gentle drying of a fresh baker's yeast (i.e., a baker's yeast between about 30% and about 35% dry matter) until the desired dry matter and a freezing by fluidization. The frozen intermediate active dry yeasts preferably have the following properties:

very good performance in tests $A_1$ $A_5$ and $A_6$ carried out with the fermentometer of Burrows and Harrison, i.e.,

| | |
|---|---|
| in test $A_1$ | gas release between 170 ml and 190 ml in two hours |
| in test $A_5$ | gas release between 110 ml and 130 ml in two hours |
| in test $A_6$ | gas release between 115 ml and 140 ml in two hours. | they are resistant to the stress caused by freezing when they are used in sweet frozen doughs, i.e., when they are used for the making of sweet Danish pastry doughs comprising 18% sucrose with respect to the flour used and comprising fats, the following characteristics are obtained:
on the one hand, the total gas release recorded with the zymotachygraphe Chopin® on a dough piece frozen and thawed after at least 100 days is higher by at least 20% than the total gas release recorded under the same conditions when using the same amount of yeast dry matter of a conventional control fresh yeast obtained starting from strain CNCM I-2412 on the other hand, the proof time of the said sweet Danish pastry doughs, frozen and thawed after at least 100 days is lower by at least 10% than that measured under the same conditions when using the same amount of yeast dry matter issued of the said conventional control fresh yeast.
they do not give rise to the appearance of bad taste or of off-flavors in the presence of cinnamon.

The new frozen intermediate active dry yeasts in fine free flowing particles can contain free flowing agents or anticaking agents as silica and silicates. It can also contain drying processing aids and/or rehydration agents such as sorbitan monostearate, gums, carboxy-methyl-cellulose.

The new frozen intermediate active dry yeasts according to the invention have the advantage of maintaining their initial properties for at least 6 months, and more preferably one year.

In other words the present invention relates to new baker's yeasts in the form of particles of frozen active dry yeast having an intermediate dry matter, i.e., a dry matter between 70% and 80%, preferably between 72% and 78%. Preferably the new baker's yeasts according to the invention in the form of frozen active dry yeast are obtained or obtainable by a process comprising the use as starting strain of one of the strains belonging to the group of the strains CNCM I-2421 and I-2422 and of the similar strains to these two strains CNCM I-2421 and I-2422 and of the baker's yeast strains obtained by inactivation of the PAD1 gene(s). Still preferably the process comprises a discontinuous inflow of molasses during the whole or part of the last cycle of multiplication. Still more preferably the new baker's yeasts according to the invention, in the form of frozen intermediate dry yeasts, have the hereabove defined gas releases in hereabove defined tests $A_1$, $A_5$ and $A_6$.

The present invention also relates to a process for the preparation of baker's yeasts comprising the use as starting strain of one of the strains of the group comprising the strains deposited according to the Budapest Convention with the "Collection Nationale de Cultures de Microorganismes", Institut Pasteur, 28 rue du Docteur Roux, 75724 PARIS CEDEX 15, under the numbers I-2421 and I-2422.

The present invention also relates to a process for the preparation of baker's yeasts comprising the use as starting strain of one of the strains selected from the group of the strains similar to the two strains I-2421 and I-2422 and the baker's yeast strains obtained by clean inactivation of the PAD1 gene(s).

Preferably in the process, the strain chosen among the group comprising the strains I-2421 and I-2422 and the strains similar to the two strains I-2421 and I-2422 and the hereabove defined strains obtained by clean inactivation of the PAD1 gene(s) is cultivated according to a fed-batch process comprising a discontinuous inflow of molasses during the whole or part of the last cycle of cultivation, i.e., during the last hours before the yielding of the yeast cells in order to obtain commercial cream yeast, fresh compressed or crumbled yeast, active dry yeast, intermediate frozen active dry yeast.

In fact, on the one hand the process according to the present invention for the preparation of new baker's yeasts according to the invention is novel, due to the use of a selected starting strain as hereabove disclosed, and on the other hand it can use the techniques conventionally used in the manufacture of baker's yeasts. However, preferably a cultivation process comprising a discontinuous inflow of molasses is used.

Concerning any details relating to these techniques, reference is made to the manual "YEAST TECHNOLOGY", Reed and Peppler, The AVI PUBLISHING, 1973, or to the second edition of that manual by Reed and Nagodawithana, An AVI book published by VAN NOSTRAND REINHOLD, 1991, which are incorporated by reference or still preferably to U.S. Pat. Nos. 4,328,250, 4,396,632 and 5,741,695 and to the UK Patent 1,539,211, and to the European Patent No. 0 237 427 B2 or the Australian patent No. 609030, the entire disclosures of which are also incorporated by reference.

The present invention relates also to new baker's yeasts obtained or able to be obtained (=obtainable) according to the hereabove disclosed processes.

The present invention relates finally to the use of baker's yeasts according to the invention for the manufacture of bread-making doughs aromatized (flavored) with cinnamon and/or for the manufacture of frozen dough pieces especially on the basis of sweetened doughs. Notably, it relates on the one hand to a process for the manufacture of breadmaking doughs aromatized with cinnamon, and on the other hand to a process for the manufacture of frozen dough pieces, preferably sweet frozen dough pieces, comprising the use of new baker's yeasts according to the present invention. Preferably the invention relates to the said dough making processes comprising the use of a baker's yeast belonging to the group of the new baker's yeasts having good general performance in not delayed bread-makings, resistant with respect to the stress caused by freezing when they are used in sweetened doughs, and not giving rise to the appearance of off-flavors in the presence of cinnamon and of the new baker's yeasts obtained or obtainable by the process comprising the use as starting strain of one of the strains of the group comprising the strains CNCM I-2421 and I-2422, and the similar strains to these two strains, i.e., the strains sharing all the common properties to the said strains I-2421 and I-2422 and/or which are able to be selected as disclosed hereabove, and the baker's yeast strains obtained by clean inactivation of the PAD1 gene(s), being understood in a general manner that preferably these modified or mutated baker's yeast strains are also resistant to the stress caused by freezing, and still preferably pass successfully the three series of selection tests hereabove disclosed. Preferably, these new baker's yeasts are in the form of frozen intermediate active dry yeasts.

The invention claimed is:
1. A baker's yeast composition which:
has good general performance in bread-making processes that do not comprise a freezing or a deep-freezing step, wherein said good general performance is determined by gas release results according to fermentometer tests $A_1$, $A_5$ and $A_6$ carried out with a Burrows and Harrison fermentometer, wherein the following gas releases in fermentometer tests $A_1$, $A_5$, $A_6$ are provided:
test $A_1$, at least 150 ml in two hours,
test $A_5$, at least 90 ml in two hours,
test $A_6$, at least 80 ml in two hours
is resistant to stress caused by freezing when used in sweetened doughs, and which is obtained by a cultivation process for manufacturing said baker's yeast composition, comprising cultivating a starting yeast strain selected from the group consisting of:
isolated yeast strains deposited according to the Budapest Convention with the "Collection Nationale de Cultures de Microorganisms", Institut Pasteur, under the numbers I-2421 (CNCM I-2421) and I-2422 (CNCM I-2422) and
isolated or recombinant baker's yeast strains obtained by clean inactivation of PAD1 gene(s) in a strain of a baker's yeast which is resistant to stress caused by freezing.
2. The baker's yeast composition according to claim 1:
wherein said gas release results based upon fermentometer tests $A_1$, $A_5$ and $A_6$ carried out with a Burrows and Harrison fermentometer are at least equivalent to gas release results obtained with a control yeast produced by a cultivation process for manufacturing said control yeast, wherein the control yeast is obtained by cultivating an isolated strain deposited under the number I-2412 (CNCM I-2412),
and wherein the baker's yeast composition, when used to produce dough having a formulation of sweet Danish pastries, comprising 18% sugar by weight with respect to a total amount of flour, whereby said dough is frozen for 100 days at −20° C. and thereafter thawed,
provides a total gas release measured with a zymotachygraphe for 2 hours and 30 minutes at 27° C., of at least 20% higher than said control yeast in a dough of the same formulation and frozen and thawed under the same conditions, and
provides a proof time of said dough measured at 35° C. of at least 10% lower than the proof time obtained with said control yeast in a dough of the same formulation and frozen and thawed under the same conditions.
3. The baker's yeast composition according to claim 1, wherein said cultivation process comprises two or more consecutive cycles of cultivation and a discontinuous inflow of molasses is provided during the whole or part of the last cycle of cultivation.
4. The baker's yeast composition according to claim 1 wherein said baker's yeast composition is in the form of a frozen active intermediate dry yeast composition having between 70 and 80% dry matter.
5. The baker's yeast composition according to claim 1 wherein said baker's yeast composition is in the form of a frozen active intermediate dry yeast composition having between 70 and 80% dry matter and providing the following gas releases in fermentometer tests $A_1$, $A_5$, $A_6$ carried out with a Burrows and Harrison fermentometer:
test $A_1$ 170 ml to 190 ml in two hours,
test $A_5$ 110 ml to 130 ml in two hours,
test $A_6$ 115 ml to 140 ml in two hours.
6. The baker's yeast composition of claim 1, which does not produce bad taste and off flavors in the presence of cinnamon, as evidenced by the presence of cinnamic acid and/or by the presence of styrene in a solution fermented in the presence of cinnamic acid.
7. The baker's yeast composition according to claim 2, which when used to produce the dough having a formulation of sweet Danish pastries, comprising 18% sugar by weight with respect to a total amount of flour, whereby said dough is frozen for 100 days at −20° C. and thereafter thawed,
provides a total gas release measured with a zymotachygraphe for 2 hours and 30 minutes at 27° C. of at least 30% higher than the control yeast in a dough of the same formulation and frozen and thawed under the same conditions, and
provides a proof time of said dough measured at 35° C. of at least 15% lower than the proof time obtained with said control yeast in a dough of the same formulation and frozen and thawed under the same conditions.
8. The baker's yeast composition according to claim 2 which when used to produce the dough having a formulation of sweet Danish pastries, comprising 18% sugar by weight with respect to a total amount of flour, whereby said dough is frozen for 100 days at −20° C. and thereafter thawed,
provides a total gas release measured with a zymotachygraphe during 2 hours and 30 minutes at 27° C. of at least 40% higher than the control yeast in a dough of the same formulation and frozen and thawed under the same conditions, and
provides a proof time of said dough measured at 35° C. of at least 20% lower than the proof time obtained with said control yeast in a dough of the same formulation and frozen and thawed under the same conditions.
9. The baker's yeast composition according to claim 4, wherein said baker's yeast composition is in the form of a frozen intermediate active dry yeast composition having between 72 and 78% dry matter.
10. The baker's yeast composition according to claim 4, wherein said baker's yeast composition is in the form of a frozen intermediate active dry yeast composition having between 74 and 78% dry matter.
11. The baker's yeast composition according to claim 5, wherein said baker's yeast composition is in the form of a frozen intermediate active dry yeast composition having between 72 and 78% dry matter.
12. A baker's yeast composition obtained by a cultivation process for the manufacture of said baker's yeast composition, comprising cultivating a starting strain, wherein said starting strain is an isolated strain deposited according to the Budapest Convention with the "Collection Nationale de Cultures de Microorganismes", Institut Pasteur, under the number I-2421 (CNCM I-2421).
13. A baker's yeast composition obtained by a cultivation process for the manufacture of said baker's yeast composition comprising, cultivating a starting strain, wherein said starting strain is an isolated strain deposited according to the Budapest Convention with the "Collection Nationale de Cultures de Microorganismes", Institut Pasteur, under the number I-2422 (CNCM I-2422).
14. A baker's yeast composition obtained by a cultivation process for the manufacture of said baker's yeast composition comprising cultivating a starting strain, wherein said starting strain is an isolated or recombinant baker's yeast strain, which is obtained by clean inactivation in a strain of a baker's yeast which is resistant to stress caused by freezing of PAD1 gene(s) encoding phenylacrylic acid decarboxylase, wherein said clean inactivation is a modification which cuts out expression of inactivated genes without leading to expression of a heterologous gene.

15. A baker's yeast composition obtained by a cultivation process for the manufacture of said baker's yeast composition comprising:
  cultivating a starting strain selected from the group consisting of:
    isolated yeast strains deposited according to the Budapest Convention with the "Collection Nationale de Cultures de Microorganismes", Institut Pasteur, under the numbers I-2421 (CNCM I-2421) and I-2422 (CNCM I-2422) and
    isolated or recombinant baker's yeast strains obtained by clean inactivation of PAD1 gene(s)
  wherein said cultivation process comprises two or more consecutive cycles of cultivation wherein a discontinuous inflow of molasses is provided during the whole or part of the last cycle of multiplication of said starting strain.

16. The baker's yeast composition according to claim 15, wherein said baker's yeast composition is in the form of a frozen intermediate active dry yeast composition having between 70 and 80% dry matter.

17. A baker's yeast composition in the form of particles of intermediate frozen active dry yeast having between 70% and 80% dry matter and which
  has good general performance in bread-making processes that do not comprise a freezing or a deep-freezing step, wherein said good general performance is determined by gas release results according to fermentometer tests $A_1$, $A_5$ and $A_6$ carried out with a Burrows and Harrison fermentometer
  is resistant to stress caused by freezing when used in sweetened doughs,
  and which provides the following gas releases in fermentometer test $A_1$, $A_5$ and $A_6$ carried out using a Burrows and Harrison fermentometer:
  test $A_1$ 170 ml to 190 ml in two hours,
  test $A_5$ 110 ml to 130 ml in two hours,
  test $A_6$ 115 ml to 140 ml in two hours,
  and which are obtained by a process comprising:
  (1) using as a starting strain in a cultivation process for the manufacture of said yeast composition, a yeast strain selected from the group consisting of:
    isolated strains deposited according to the Budapest Convention with the "Collection Nationale de Cultures de Microorganismes", Institut Pasteur, under the numbers I-2421 (CNCM I-2421) and I-2422 (CNCM I-2422), and
    isolated or recombinant baker's yeast strains obtained by clean inactivation of the PAD1 gene(s) in a strain of a baker's yeast which is resistant to stress caused by freezing, and
  (2) cultivating said starting strain according to said cultivation process for the manufacture of said baker's yeast composition, said cultivation process comprising two or more consecutive cycles of cultivation wherein a discontinuous inflow of molasses is provided during the whole or part of the last cycle of cultivation of said starting strain.

18. The baker's yeast composition according to claim 17 wherein said baker's yeast composition is in the form of a frozen intermediate active dry yeast composition having between 72 and 78% dry matter.

19. The baker's yeast composition of claim 17, which does not produce bad taste and off flavors in the presence of cinnamon, as evidenced by the presence of cinnamic acid and/or by the presence of styrene in a solution fermented in the presence of cinnamic acid.

20. An isolated baker's yeast strain deposited according to the Budapest Convention with the "Collection Nationale de Cultures de Microorganismes", under the number I-2421 (CNCM I-2421).

21. An isolated baker's yeast strain deposited according to the Budapest Convention with the "Collection Nationale de Cultures de Microorganismes", Institut Pasteur, under the number I-2422 (CNCM I-2422).

22. An isolated or recombinant baker's yeast strain obtained by clean inactivation of the PAD1 gene(s) in a strain of baker's yeast.

23. A process for the preparation of a baker's yeast composition comprising a cultivation process for the manufacture of said yeast composition comprising cultivating a starting strain which is an isolated strain deposited according to the Budapest Convention with the "Collection Nationale de Cultures de Microorganismes", Institut Pasteur, under the number I-2421 (CNCM I-2421) and harvesting to provide said baker's yeast composition.

24. The process for the preparation of a baker's yeast composition according to claim 23 wherein said starting strain is cultivated according to a process comprising two or more consecutive cycles of cultivation wherein a discontinuous inflow of molasses is provided during the whole or part of the last cycle of cultivation.

25. A process for the preparation of a baker's yeast composition comprising a cultivation process for the manufacture of said yeast composition comprising cultivating a starting strain which is an isolated strain deposited according to the Budapest Convention with the "Collection Nationale de Cultures de Microorganismes", Institut Pasteur, under the number I-2422 (CNCM I-2422) and harvesting to provide said baker's yeast composition.

26. The process for the preparation of a baker's yeast composition according to claim 25 wherein said starting strain is cultivated according to a process comprising two or more consecutive cycles of cultivation wherein a discontinuous inflow of molasses is provided during the whole or part of the last cycle of cultivation.

27. A process for the preparation of a baker's yeast composition comprising a cultivation process for the manufacture of said baker's yeast comprising cultivating a starting strain which is a baker's yeast strain obtained by clean inactivation of the PAD1 gene(s) in a baker's yeast which is resistant to stress caused by freezing and harvesting to provide said baker's yeast composition.

28. The process for the preparation of a baker's yeast composition according to claim 27 wherein said starting strain is cultivated according to a process comprising two or more consecutive cycles of cultivation wherein a discontinuous inflow of molasses is provided during the whole or part of the last cycle of cultivation.

29. A baker's yeast composition comprising yeast strains selected from the group consisting of isolated yeast strains deposited according to the Budapest Convention with the "Collection Nationale de Cultures de Microorganismes", Institut Pasteur, under the numbers I-2421 (CNCM I-2421) and I-2422 (CNCM I-2422) and baker's yeast strains obtained by clean inactivation of PAD1 gene(s) in a strain of a baker's yeast which is resistant to stress caused by freezing.

30. The baker's yeast composition of claim 29, which:
has good general performance in bread-making processes that do not comprise a freezing or deep-freezing step, wherein said good general performance is determined by gas release results according to fermentometer tests $A_1$, $A_5$ and $A_6$ carried out with a Burrows and Harrison fermentometer wherein the following gas releases in fermentometer tests $A_1$, $A_5$, $A_6$ are provided:
test $A_1$, at least 150 ml in two hours,
test $A_5$, at least 90 ml in two hours,
test $A_6$, at least 80 ml in two hours and
is resistant to stress caused by freezing when used in sweetened doughs.

31. The baker's yeast composition of claim 30:
wherein said gas release results based upon fermentometer tests $A_1$, $A_5$ and $A_6$ carried out with a Burrows and Harrison fermentometer are at least equivalent to gas release results obtained with a control yeast produced by a cultivation process for manufacturing said control yeast, by cultivating an isolated strain deposited under the number I-2412 (CNCM I-2412),
and wherein the baker's yeast composition, when used to produce dough having a formulation of sweet Danish pastries, comprising 18% sugar by weight with respect to a total amount of flour, whereby said dough is frozen for 100 days at −20° C. and thereafter thawed,
provides a total gas release measured with a zymotachygraphe for 2 hours and 30 minutes at 27° C., of at least 20% higher than said control yeast in a dough of the same formulation and frozen and thawed under the same conditions, and
provides a proof time of said dough measured at 35° C. of at least 10% lower than the proof time obtained with said control yeast in a dough of the same formulation and frozen and thawed under the same conditions.

32. The baker's yeast composition of claim 30, wherein said baker's yeast composition is in the form of a frozen active intermediate dry yeast composition having between 70 and 80% dry matter.

33. The baker's yeast composition of claim 30 wherein said baker's yeast composition is in the form of a frozen active intermediate dry yeast composition having between 70 and 80% dry matter and providing the following gas releases in fermentometer tests $A_1$, $A_5$, $A_6$ carried out with a Burrows and Harrison fermentometer
test $A_1$ 170 ml to 190 ml in two hours,
test $A_5$ 110 ml to 130 ml in two hours,
test $A_6$ 115 ml to 140 ml in two hours.

34. The baker's yeast composition of claim 33, in the form of particles of intermediate frozen active dry yeast between 70 and 80% dry matter.

35. The baker's yeast composition of claim 30, which when used to produce the dough having a formulation of sweet Danish pastries, comprising 18% sugar by weight with respect to a total amount of flour, whereby said dough is frozen for 100 days at −20° C. and thereafter thawed,
provides a total gas release measured with a zymotachygraphe for 2 hours and 30 minutes at 27° C. of at least 30% higher than a control yeast produced by a cultivation process for manufacturing said control yeast, by cultivating an isolated strain deposited under the number I-2412 (CNCM I-2412) in a dough of the same formulation and frozen and thawed under the same conditions, and
provides a proof time of said dough measured at 35° C. of at least 15% lower than the proof time obtained with said control yeast in a dough of the same formulation and frozen and thawed under the same conditions.

36. The baker's yeast composition of claim 30, which when used to produce the dough having a formulation of sweet Danish pastries, comprising 18% sugar by weight with respect to a total amount of flour, whereby said dough is frozen for 100 days at −20° C. and thereafter thawed,
provides a total gas release measured with a zymotachygraphe during 2 hours and 30 minutes at 27° C. of at least 40% higher than a control yeast produced by a cultivation process for manufacturing said control yeast, by cultivating an isolated strain deposited under the number I-2412 (CNCM I-2412) in a dough of the same formulation and frozen and thawed under the same conditions, and
provides a proof time of said dough measured at 35° C. of at least 20% lower than the proof time obtained with said control yeast in a dough of the same formulation and frozen and thawed under the same conditions.

37. The baker's yeast composition of claim 32, wherein said baker's yeast is in the form of a frozen intermediate active dry yeast composition having between 72 and 78% dry matter.

38. The baker's yeast composition of claim 32, wherein said baker's yeast is in the form of a frozen intermediate active dry yeast composition having between 74 and 78% dry matter.

39. The baker's yeast composition of claim 33, wherein said baker's yeast is in the form of a frozen intermediate active dry yeast composition having between 72 and 78% dry matter.

40. The baker's yeast composition of claim 34, wherein said baker's yeast is in the form of a frozen intermediate active dry yeast composition having between 72 and 78% dry matter.

41. The baker's yeast composition of claim 30, which does not produce bad taste and off flavors in the presence of cinnamon, as evidenced by the presence of cinnamic acid and/or by the presence of styrene in a solution fermented in the presence of cinnamic acid.

42. An isolated or recombinant baker's yeast strain obtained by clean inactivation of PAD 1 gene(s) in a strain of baker's yeast and resistant to the stress caused by freezing.

43. A process for the manufacture of bread-making dough aromatized with cinnamon comprising:
providing a baker's yeast obtained by a process comprising the use as starting strain of a strain selected from the group consisting of the strains deposited according to the Budapest Convention with the "Collection Nationale de Cultures de Microorganismes", Institut Pasteur, under the numbers I-2421 (CNCM I2421) and I-2422 (CNCM I2422) and baker's yeast strains obtained by clean inactivation of PAD1 gene(s), and
forming said dough.

44. The process for the production of bread-making dough according to claim 43, wherein the baker's yeast is in the form of a frozen intermediate dry yeast product.

45. A process for the manufacture of frozen sweetened dough pieces using a baker's yeast obtained by a process comprising:

providing a starting strain of a strain selected from the group consisting of the strains deposited according to the Budapest Convention with the "Collection Nationale de Cultures de Microorganismes", Institut Pasteur, under the numbers I-2421 (CNCM I2421) and I-2422 (CNCM I2422) and baker's yeast strains obtained by clean inactivation of PAD1 gene(s); and forming said dough pieces.

* * * * *